United States Patent [19]

Min et al.

[11] Patent Number: 5,690,686
[45] Date of Patent: Nov. 25, 1997

[54] ATRIAL DEFIBRILLATION METHOD

[75] Inventors: Xiaoyi Min, Plymouth; Luc R. Mongeon, Minneapolis; Rahul Mehra, Stillwater; Kenneth M. Anderson, Bloomington, all of Minn.

[73] Assignee: Medtronic, Inc., Minneapolis, Minn.

[21] Appl. No.: 640,380

[22] Filed: Apr. 30, 1996

[51] Int. Cl.$^6$ ................................................. A61N 1/39
[52] U.S. Cl. ................................................................ 607/5
[58] Field of Search ............................................ 607/5, 4

[56] References Cited

U.S. PATENT DOCUMENTS

| | | |
|---|---|---|
| 3,738,370 | 6/1973 | Charms . |
| 3,952,750 | 4/1976 | Mirowski . |
| 4,161,952 | 7/1979 | Kinney . |
| 4,316,472 | 2/1982 | Mirowski . |
| 4,355,646 | 10/1982 | Kallok . |
| 4,375,817 | 3/1983 | Engle . |
| 4,384,584 | 5/1983 | Chen . |
| 4,481,953 | 11/1984 | Gold . |
| 4,577,633 | 3/1986 | Berkovits . |
| 4,587,970 | 5/1986 | Holley . |
| 4,708,145 | 11/1987 | Tacker, Jr. . |
| 4,726,380 | 2/1988 | Vollmann . |
| 4,727,877 | 3/1988 | Kallok . |
| 4,800,883 | 1/1989 | Winstrom . |
| 4,830,006 | 5/1989 | Haluska . |
| 4,880,005 | 11/1989 | Pless . |
| 4,922,927 | 5/1990 | Fine . |
| 4,934,049 | 6/1990 | Kiekhafer . |
| 4,949,719 | 8/1990 | Pless . |
| 4,953,551 | 9/1990 | Mehra . |
| 5,005,587 | 4/1991 | Scott . |
| 5,014,696 | 5/1991 | Mehra ........................ 607/5 |
| 5,042,143 | 8/1991 | Holleman . |
| 5,099,838 | 3/1992 | Bardy . |
| 5,107,834 | 4/1992 | Ideker et al. ................. 607/5 |
| 5,117,824 | 6/1992 | Keimel . |
| 5,143,089 | 9/1992 | Alt . |
| 5,163,427 | 11/1992 | Keimel . |
| 5,165,403 | 11/1992 | Mehra . |
| 5,188,105 | 2/1993 | Keimel . |
| 5,269,298 | 12/1993 | Adams . |
| 5,292,338 | 3/1994 | Bardy . |
| 5,306,291 | 4/1994 | Kroll et al. ................... 607/5 |
| 5,314,430 | 5/1994 | Bardy . |
| 5,324,309 | 6/1994 | Kallok ........................ 607/5 |
| 5,376,103 | 12/1994 | Anderson et al. ........... 607/5 |
| 5,431,683 | 7/1995 | Bowald et al. .............. 607/5 |
| 5,549,642 | 8/1996 | Min et al. .................... 607/5 |

OTHER PUBLICATIONS

Arzbaecher et al. "Automatic Tachycardia Recognition", PACE, vol. 7 May–Jun., 1984 Part II p. 541.

Olson et al., "Onset and Stability for Ventricular Tachyarrhythmia Detection in an Implantable Pacer–Cardioverter–Defibrillator", Computers In Cardiology, Oct. 7–10, 1986, p. 167.

Jain et al., "Elective Countershock in Artrial Fibrillation with an Intracardiac Electrode–A Preliminary Report" Journal Assoc. Physicians Of India 18. (1970) 821.

Blanc, et al., "Safety and Feasibility of Transvenous Cardioversion in Atrial Tachycardia", p. 1526.

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

A method and apparatus for treating atrial tachyarrhythmias, particularly atrial fibrillation. High energy pulses are delivered between electrodes located in the right atrium/SVC, the left pectoral region and the coronary sinus/great vein, with the left pectoral and coronary sinus/great vein electrodes connected in common. Optionally a ventricular electrode may also be employed in conjunction with one or more of the other listed electrodes to accomplish ventricular cardioversion or defibrillation.

4 Claims, 4 Drawing Sheets

5,690,686

ATRIAL DEFIBRILLATION METHOD

BACKGROUND OF THE INVENTION

The present invention relates to medical stimulators and leads generally, and more particularly to implantable defibrillators and defibrillation leads.

Currently available implantable ventricular defibrillators typically employ epicardial or subcutaneous patch electrodes, alone, or in conjunction with one or more transvenous electrodes. Multi-electrode ventricular defibrillation systems are disclosed in U.S. Pat. No. 4,727,877 issued to Kallok, U.S. Pat. No. 4,708,145 issued to Tacker, et al., and as disclosed in U.S. Pat. No. 5,099,838, issued to Bardy. Other endocardial defibrillation electrodes are disclosed in U.S. Pat. No. 4,481,953 issued to Gold et al., U.S. Pat. No. 4,161,952 issued to Kinney, et al., U.S. Pat. No. 4,934,049 issued to Kiekhafer et al. and in U.S. Pat. No. 5,042,143 issued to Holleman, et al. The Kinney, Gold, Holleman and Kiekhafer patents all disclose endocardial defibrillation leads employing defibrillation electrodes fabricated from elongated coils of biocompatible metal, mounted exposed to the exterior of the defibrillation lead, for location in the right ventricle and other locations within the heart. The above-cited Smits patent and the Mehra application both disclose a variety of endocardial defibrillation electrodes intended for use in the atrium, ventricle and coronary sinus, all of which employ electrodes taking the form of elongated coils of conductive biocompatible metals. U.S. Pat. No. 4,922,927, issued to Fine et al. proposes the use of a ventricular defibrillation electrode system using only a right ventricular electrode and a subcutaneous electrode, which may correspond to prior art subcutaneous electrodes or may be the metal enclosure of the defibrillator.

Concurrent with the development of lead systems adapted to treat ventricular fibrillation, there has also been some work directed to the development of lead systems to treat atrial fibrillation. Synchronized cardioversion using two electrodes located on a lead located in the right atrium is disclosed in U.S. Pat. No. 3,738,370, issued to Charms. A later system is disclosed in U.S. Pat. No. 3,952,750, issued to Mirowski et al., employing one electrode in the atrium and presumably a second electrode at an unspecified location. Neither of these references discloses a specific embodiment for the electrodes located in the atrium.

An electrode lead system specifically designed for atrial defibrillation is disclosed in the article "Elective Counter-shock in Atrial Fibrillation With an Intracardiac Electrode—A Preliminary Report, by Jain, et al., published in the *Journal of the Association of Physicians of India*, Vol. 18, pp 821–824, 1970. This lead was provided with a 10 mm silver electrode for location in the right atrium and was tested in conjunction with either a second electrode located in the right atrium or a second, cutaneous electrode located on the left side of the chest wall. A second electrode system specifically designed for use in atrial cardioversion is disclosed in the article "Safety and feasibility of transvenous cardioversion in atrial tachycardia", by Blanc et al., published in *Cardiac Pacing*, edited by Gomez, Futura Pub. Co., 1985, pp 1526–1529. This electrode system employed a single lead with electrodes located in the atrium and pulmonary artery. More recently, the use of electrodes located in the right atrium and coronary sinus/great vein for atrial defibrillation has been disclosed in U.S. Pat. No. 5,165,403 issued Nov. 24, 1992 to Mehra. Delivery of atrial defibrillation pulses between the right ventricle and a subcutaneous electrode is disclosed in U.S. Pat. No. 5,292,338, issued Mar. 8, 1994 to Bardy. Delivery of atrial defibrillation pulse between a coronary sinus electrode and a subcutaneous electrode is disclosed in U.S. Pat. No. 5,314,430, issued on May 24, 1994 to Bardy. The cited Mehra patent and the two cited Bardy patents are hereby incorporated herein by reference in their entireties.

In the context of an implantable atrial defibrillator, it is especially desirable to reduce defibrillation energy thresholds. Because it is anticipated that such devices will likely deliver defibrillation pulses more frequently than implantable ventricular defibrillators, reduced energy thresholds are necessary to achieve a device having acceptable longevity. In addition, as the patients receiving the defibrillation pulses will generally be conscious, frequent painful shocks are believed to be undesirable, if not unacceptable. This factor further reduces the desirable atrial defibrillation threshold to about 1 Joule or less. Despite the amount of activity in this area, as reflected in the references cited above, the goal of a defibrillation lead system which will generally accomplish such low defibrillation thresholds has not been accomplished. The right atrium to coronary sinus/great vein pathway, disclosed in the Mehra '403 patent accomplishes this goal in some patients, but in others requires substantially higher energy levels.

SUMMARY OF THE INVENTION

The present invention is directed toward the provision of a defibrillator and defibrillation electrode system particularly optimized for use in defibrillation or cardioversion of the atrium at low energy levels. The electrode system includes a coronary sinus/great vein electrode, an elongated right atrial/superior vena cava (SVC) electrode and a subcutaneous electrode which preferably takes the form of a conductive portion of the housing of an implantable atrial defibrillator. The present invention is preferably practiced in a combined atrial/ventricular defibrillator, which also employs a ventricular defibrillation electrode, and which delivers an asymmetrical biphasic capacitive discharge pulse, as disclosed in U.S. Pat. No. 4,953,551, issued on Sep. 4, 1990 to Mehra et al., incorporated herein by reference in its entirety. During atrial cardioversion or defibrillation, the coronary sinus/great vein electrode are preferably connected in common with the subcutaneous electrode, and a biphasic pulse delivered between these coupled electrodes and the right atrial/SVC electrode. Alternatively, atrial cardioversion or defibrillation pulses may be delivered sequentially between the right atrial/SVC electrode and the CS/great vein electrode and between the right atrial/SVC electrode and the subcutaneous electrode. Preferably, the device is configured to perform atrial and ventricular defibrillation or cardioversion, and some or all of the electrodes employed for atrial cardioversion and defibrillation may also be employed for ventricular cardioversion or defibrillation.

DETAILED DESCRIPTION OF THE PREFERRED EMBODIMENT

Figure 1:
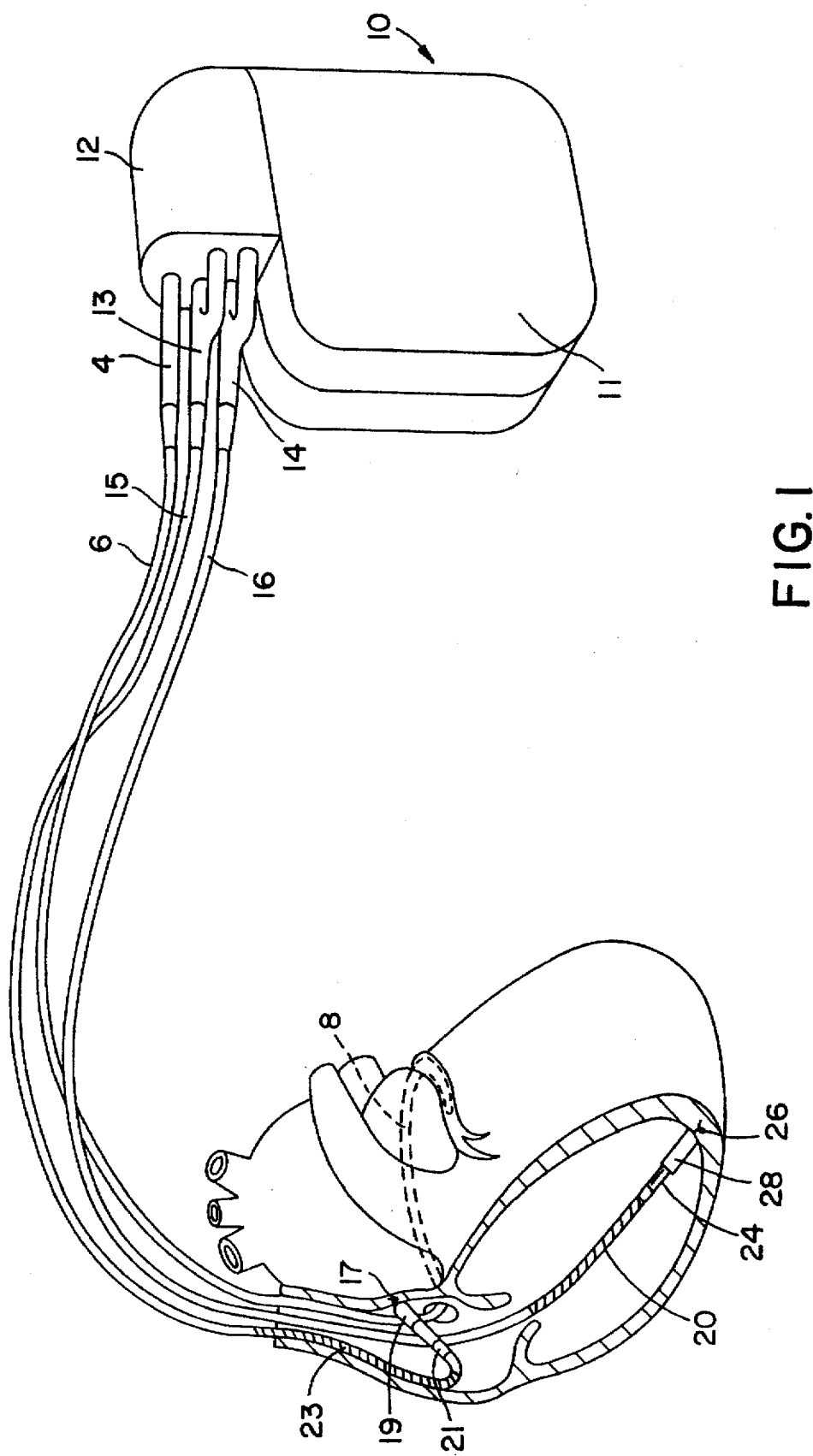
FIG. 1 illustrates a first embodiment of an implantable defibrillator and lead according to the present invention.

FIG. 1 illustrates a defibrillator and lead set according to the present invention. The ventricular lead takes the form of the lead disclosed in the above cited patents issued to Bardy, and includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding to the structure of the ventricular lead. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is 10 cm in length or greater and is configured to extend from the SVC toward the tricuspid valve. In one preferred embodiment tested by the inventors, approximately 5 cm of the right atrium/SVC electrode was located in the right atrium, with the remaining 5 cm located in the SVC. At the proximal end of the lead is a bifurcated connector 13 which carries three electrical connectors, each coupled to one of the coiled conductors.

The coronary sinus lead takes the form of the coronary sinus lead disclosed in the above cited '838 patent issued to Bardy, and includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used to defibrillate either the atria or ventricles.

It has previously been determined that the right atrial/SVC to CS/great vein defibrillation electrode system is preferable to a right atrial/SVC to subcutaneous patch system (see U.S. Pat. No. 5,165,403, issued to Mehra). More recent research conducted by the inventors has led to the conclusion that an electrode system according to the present invention, in which defibrillation energy is diverted from the right atrial/SVC to CS/great vein pulse delivery pathway nonetheless provides reduced defibrillation thresholds. As a result, the present invention is believed to provide a substantial improvement over the right atrial/SVC to coronary sinus/great vein electrode system employed in the '403 Mehra patent and the Adams patents.

The improvement of the present invention over the right atrium to coronary sinus/great vein defibrillation electrode system by the addition of the right atrial/SVC to subcutaneous defibrillation pulse pathway may seem somewhat surprising, given that the CS/great vein electrode and the subcutaneous electrodes have typically been considered to be alternatives to one another in the context of atrial defibrillation, with the subcutaneous electrode perceived as the less desirable alternative.

Figure 2:
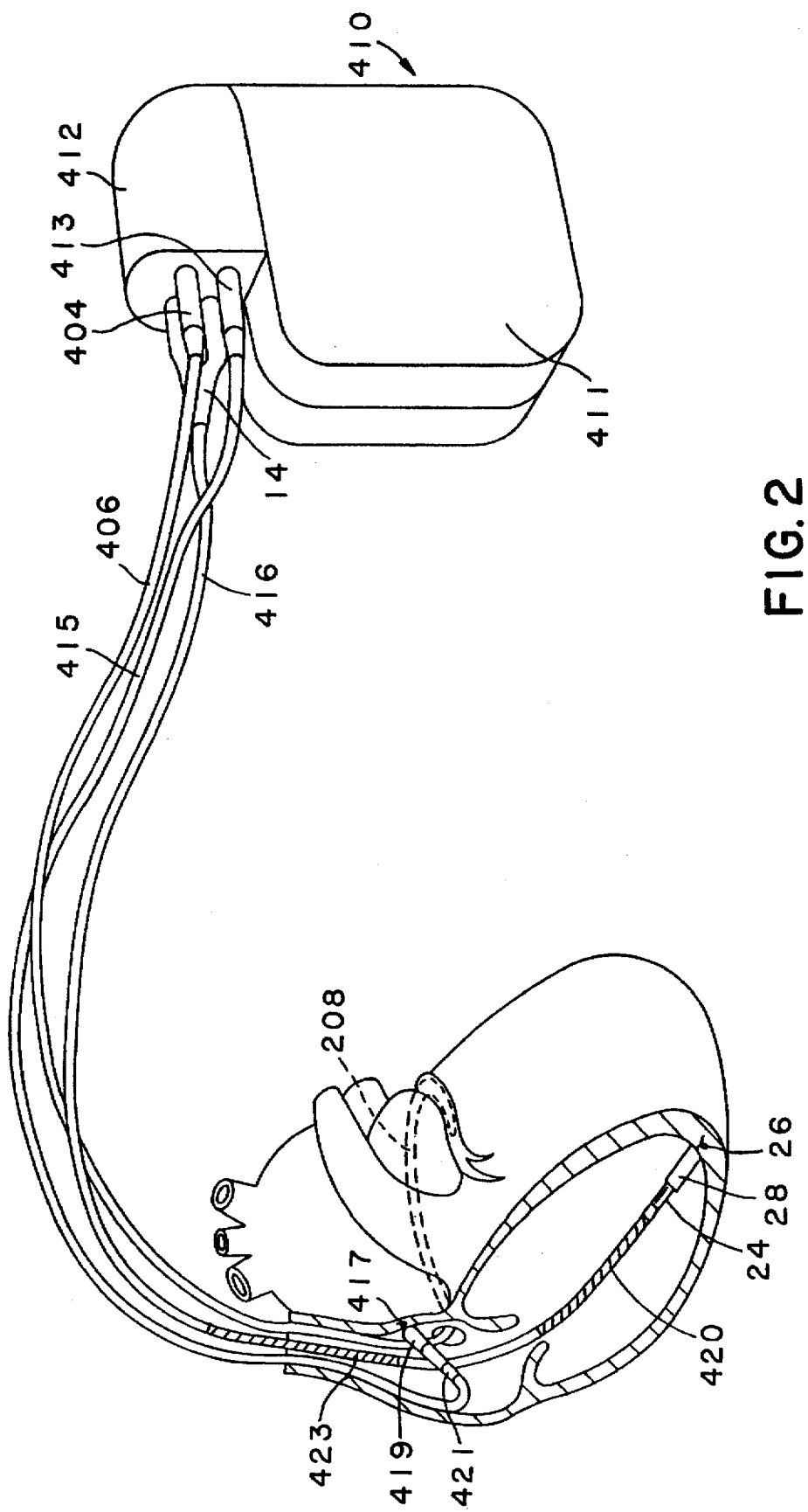
FIG. 2 illustrates a second embodiment of an implantable defibrillator and lead according to the present invention.

FIG. 2 illustrates an alternative defibrillator and lead set according to the present invention. In this embodiment, the pacemaker/cardioverter/defibrillator 410 corresponds precisely to the pacemaker/cardioverter/defibrillator 10 illustrated in FIG. 1. Only the configurations of the atrial/SVC lead and the right ventricular lead are changed. The ventricular lead includes the right atrial/SVC defibrillation electrode, and the atrial lead corresponds to a standard atrial pacing lead. The ventricular lead includes an elongated insulative lead body 16, carrying four parallel coiled conductors, mounted within a four lumen tubular insulative sheath. Located adjacent the distal end of the lead are a ring electrode 424, an extendable helix electrode 426, mounted retractably within an insulative electrode head 428, and an elongated coil electrode 420. An additional elongated coil electrode 423 is located proximal to electrode 420, spaced to allow placement in the right atrium/SVC. Each of the electrodes is coupled to one of the coiled conductors within the lead body 16. Electrodes 424 and 426 are employed for cardiac pacing and for sensing ventricular depolarizations.

At the proximal end of the lead is a bifurcated connector 414 which carries four electrical connectors, each coupled to one of the coiled conductors. The defibrillation electrodes 420 and 423 may be fabricated from platinum, platinum alloy or other materials known to be usable in implantable defibrillation electrodes and may conveniently be about 5 cm in length and about 10 cm or greater in length, respectively. The atrial/SVC lead includes an elongated insulative lead body 415, carrying two concentric coiled conductors, separated from one another by a tubular insulative sheath, corresponding to the structure of the commercially available atrial pacing leads. Located adjacent the J-shaped distal end of the lead are a ring electrode 421 and an extendable helix electrode 417, mounted retractably within an insulative electrode head 419. Each of the electrodes is coupled to one of the coiled conductors within the lead body 15. Electrodes 417 and 421 are employed for atrial pacing and for sensing atrial depolarizations. At the proximal end of the lead is a bipolar, in-line connector 413 which carries two electrical connectors, each coupled to one of the coiled conductors.

The coronary sinus lead corresponds to the coronary sinus lead illustrated in FIG. 1 and includes an elongated insulative lead body 406, carrying one coiled conductor, coupled to an elongated coiled defibrillation electrode 408. Electrode 408, illustrated in broken outline, is located within the coronary sinus and great vein of the heart. At the proximal end of the lead is a connector plug 404 which carries an electrical connector, coupled to the coiled conductor. The coronary sinus/great vein electrode 408 may be about 5 cm in length.

Figure 3:
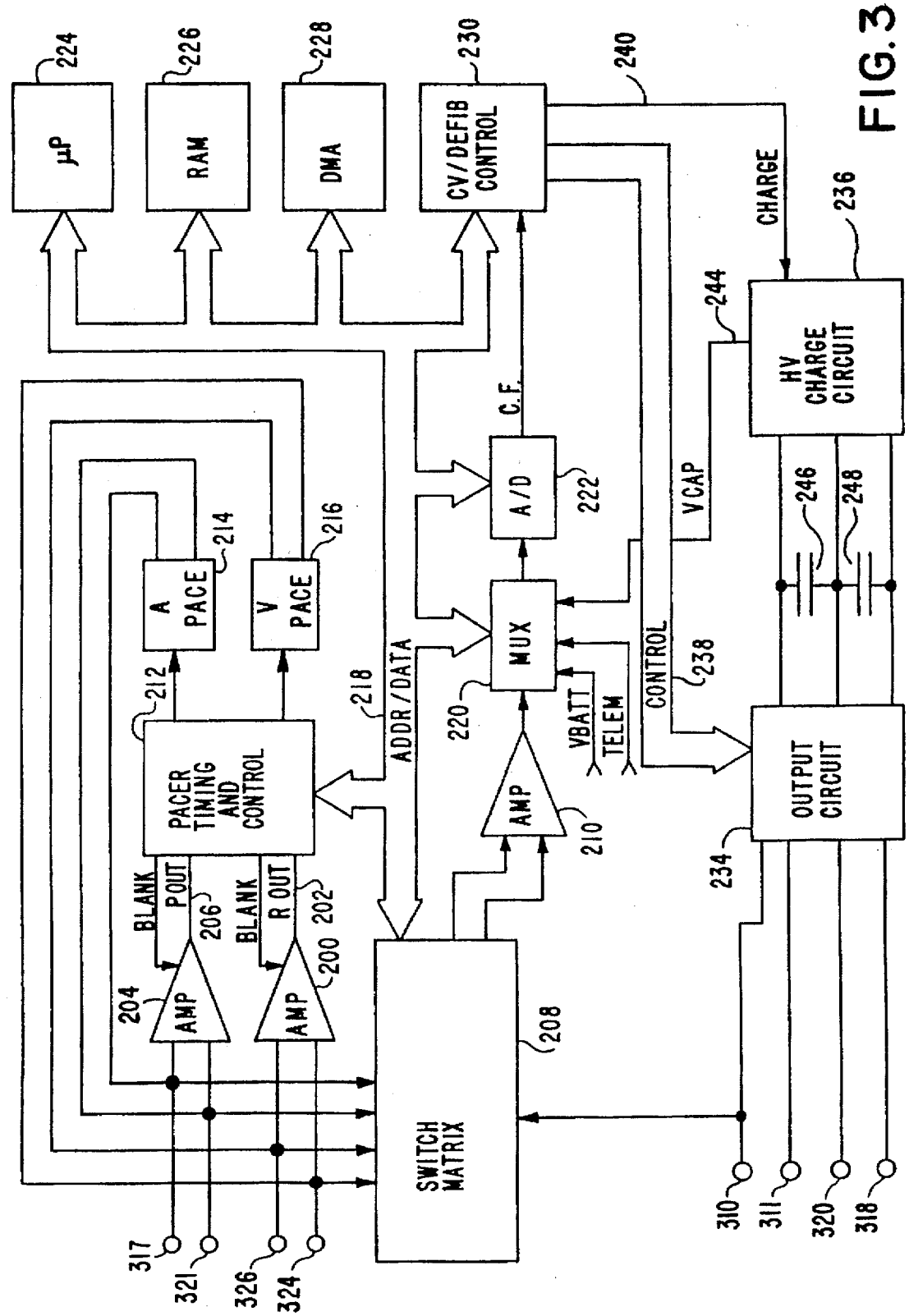
FIG. 3 illustrates a functional schematic diagram of an implantable pacemaker/cardioverter/defibrillator in which the invention may usefully be practiced in conjunction with the electrodes illustrated in FIGS. 1 and 2.

FIG. 3 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including cardioverter and defibrillators which do not provide anti-tachycardia pacing therapies.

The device is provided with an electrode system including electrodes as illustrated in FIG. 1 or FIG. 2. If the electrode configuration of FIG. 1 is employed, the correspondence to the illustrated electrodes is as follows. Optional electrode 310 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 311 corresponds to electrode 23, and is located in the right atrium and SVC. Electrode 318 corresponds to electrode 8 and is a defibrillation electrode located in the coronary sinus and great vein. Electrodes 324 and 326 correspond to electrodes 24 and 26, and are used for sensing and pacing in the ventricle. Electrodes 317 and 321 correspond to electrodes 17 and 19 and are used for pacing and sensing in the atrium.

Electrodes 310, 311, 318 and 320 are coupled to high voltage output circuit 234. High voltage output circuit 234 includes high voltage switches controlled by CV/defib control logic 230 via control bus 238. The switches within circuit 234 control which electrodes are employed and which are coupled to the positive and negative terminals of the capacitor bank including capacitors 246 and 248 during delivery of the defibrillation pulses.

Electrodes 424 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 612 and 614 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 617 and 621 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on time-out trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, and is responsive to interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et al., all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated herein in its entirety. However, one of the advantages of the present invention is that it is believed practicable in conjunction with most prior art tachycardia detection algorithms. Atrial fibrillation detection methodologies in particular are disclosed in Published PCT application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference in their entireties. In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs the an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, incorporated herein by reference in its entirety. Embodiments of appropriate systems for delivery and synchronization of atrial cardioversion and defibrillation pulses and for controlling the timing functions related to them are disclosed in more detail in U.S. Pat. No. 5,269,298 by Adams et al., issued Dec. 14, 1993 and in U.S. Pat. No. 4,316,472 by Mirowski et al., issued Feb. 23, 1982, both incorporated herein by reference in their entireties. However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In the event that, as in FIG. 1, both atrial and ventricular defibrillation are available, ventricular defibrillation may be accomplished using higher pulse energy levels than required for atrial defibrillation and may employ the same or a different electrode set. For example, electrodes 310, 311 and 318 may be employed for atrial defibrillation. One or more of electrodes 310, 311 and 318 might be employed in conjunction with electrode 320 for ventricular defibrillation. For example, electrode 311 (right atrium/SVC) may be coupled to electrode 310 (device housing) and used in conjunction with electrode 320. Alternatively, electrodes 310, 318 and 320 may be employed, with electrode 318 (coronary sinus/great vein) coupled to electrode 310.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/cardioverter/ defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 4:
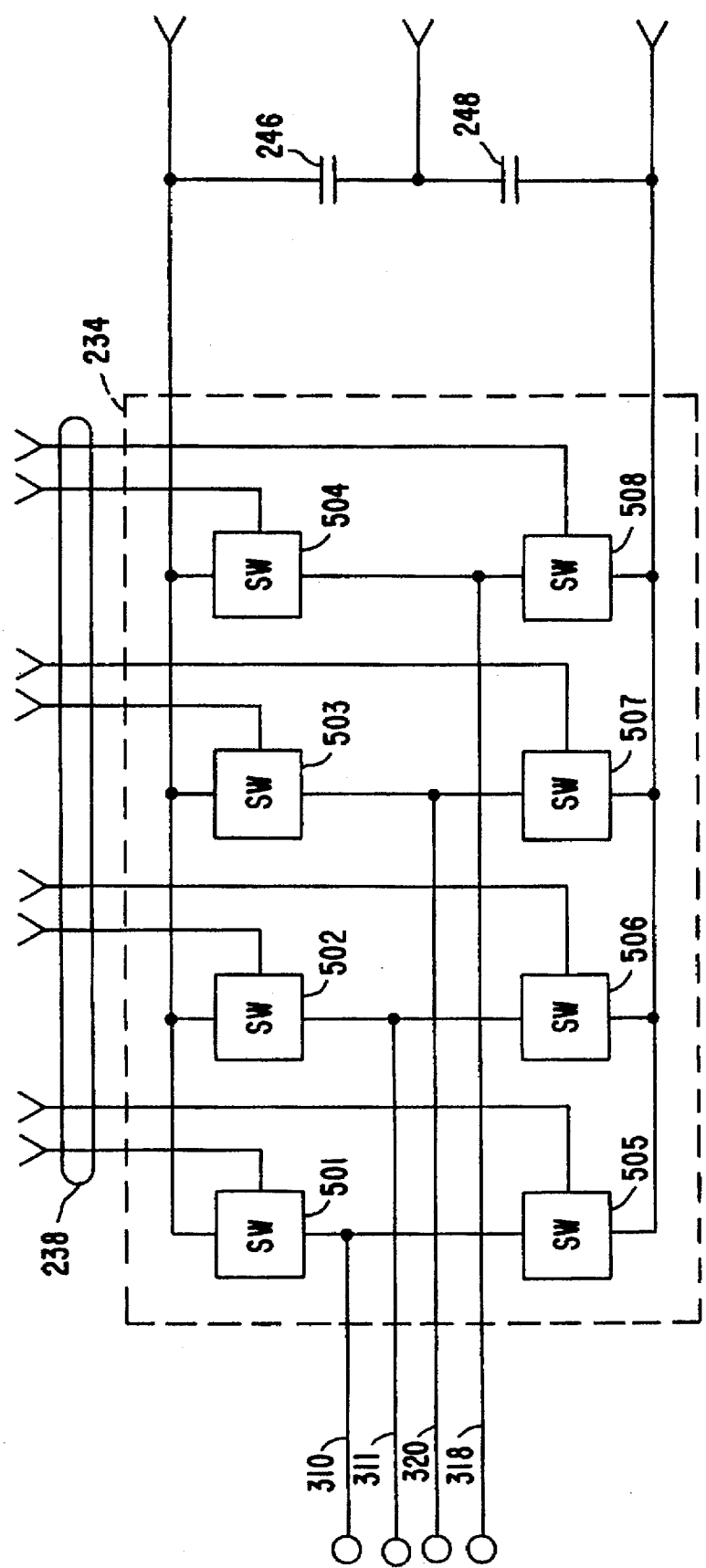
FIG. 4 illustrates a functional schematic diagram of the high voltage output circuit of the implantable pacemaker/cardioverter/defibrillator illustrated in FIG. 4.

FIG. 4 is a functional schematic diagram of switching circuitry which may be employed in high voltage output circuit 234, illustrated in FIG. 4. The circuitry includes eight high voltage switches 501, 502, 503, 504, 505, 506, 507 and 508, which are individually controlled by signals on control bus 238. These switches allow connection of any of the four electrodes 301, 311, 320 and 318 to either the positive or the negative terminal of the capacitor bank comprising capacitors 246 and 248. As illustrated, any combination of electrodes may be selected, any polarities desired may be provided, and monophasic or biphasic pulses may be delivered, depending upon control signals on control bus 238. A biphasic pulse would be provided by reversing the polarity of the connection of the capacitor bank to the selected electrodes, during the discharge of the capacitor bank. A sequential pulse regimen may similarly be provided by changing which electrodes are connected to the capacitor bank, during the discharge of the capacitor bank. In the event that a reduced set of available electrode configurations is desired, the switching circuitry may be simplified. For example, if two electrodes are hard wired together, either in the connector block or in the device housing, one set of two switches may be deleted. Correspondingly, if only atrial defibrillation is desired, using only three electrodes two sets of switches could be deleted, resulting in an output circuit employing only four switches and which corresponds to high voltage output circuits presently used in implantable ventricular defibrillators.

While the invention is disclosed above embodied in a dual chamber pacemaker/cardioverter/defibrillator, the invention may also be usefully practiced in substantially simpler devices. For example, the illustrated defibrillation electrodes may simply be coupled to an implantable atrial cardioverter as disclosed in U.S. Pat. No. 3,738,370, issued to Charms, or as disclosed in published PCT application Ser. No. US92/02829, Publication No. WO92/18198, by Adams et al, both of which are incorporated herein by reference in their entireties. A simple device of this type is believed workable in some patients. However, inclusion of the ability to detect and terminate ventricular tachycardias and fibrillation is believed of extreme importance in patients in whom delivery of atrial cardioversion or defibrillation pulses unintentionally in initiates ventricular arrhythmias.

While the defibrillation electrodes disclosed above all take the form of elongated coils, other electrode types may also be employed in conjunction with the present invention. For example, carbon fiber braids as disclosed in U.S. Pat. No. 5,143,089 issued on Sep. 1, 1992 to Alt, conductive meshes as disclosed in U.S. Pat. No. 5,005,587, issued on Apr. 9, 1991 to Scott might be employed, or defibrillation electrodes taking the form of one or more ring electrodes as disclosed in U.S. Pat. No. 4,355,646, issued on Oct. 22, 1982 to Kallok might be substituted. Similarly, it is believed that the specific electrode lengths set forth may be further refined as development of atrial defibrillation electrode systems continues. Similarly, while the electrodes employed for atrial sensing and pacing are disclosed as mounted to the atrial lead, these electrodes might alternatively take the form of ring electrodes mounted to either the ventricular lead or the coronary sinus/great vein lead. As such, the above disclosure should be considered exemplary, rather than limiting, with regard to the following claims.

While the device disclosed above is describe primarily in terms of delivering defibrillation pulses using the elongated electrodes described, it should be understood that the invention may also usefully to treat tachyarrhythmias which are not fibrillation. For example, high voltage pulses of amplitudes less than typically employed to treat fibrillation may be used to terminate ventricular and atrial tachycardias. This treatment is typically referred to as "cardioversion". The term "cardioversion is also used more broadly to include both defibrillation and delivery of high voltage pulses to terminate other tachyarrhythmias. it is this broader definition which is used in the claims which follow.

In conjunction with the above specification, we claim:

1. A method of cardioverting a patient's heart, comprising:

locating a first electrode in the coronary sinus of said patient's heart;

locating a second electrode subcutaneously in a left pectoral location in said patient's chest;

locating a third electrode in the right atrium/superior vena cava portion of said patient's heart;

sensing an occurrence of atrial tachyarrhythmia;

coupling said first electrode to said second electrode; and delivering a cardioversion pulse between said first and third electrodes and between said second and third electrodes in response to a detected occurrence of atrial tachyarrhythmia.

2. A method according to claim 1 wherein said step of delivering a cardioversion pulse further comprises coupling said first and second electrodes to one another during said pulse.

3. A method according to claim 1 or claim 2 further comprising;

locating a fourth electrode adjacent said patient's ventricle;

sensing an occurrence of ventricular tachyarrhythmia; and delivering a cardioversion pulse between one or more of said first, second and third electrodes and said fourth electrode.

4. A method according to claim 3 wherein said step of locating said fourth electrode comprises implanting a pulse generator including a housing having a conductive portion.

\* \* \* \* \*